United States Patent [19]

Belzile

[11] Patent Number: 4,540,366

[45] Date of Patent: Sep. 10, 1985

[54] ABSORBENT SWAB IMBIBER

[76] Inventor: Jean-Yves Belzile, C.P. 100, Saint-Mathieur, Canada

[21] Appl. No.: 598,578

[22] Filed: Apr. 10, 1984

[51] Int. Cl.$^3$ .............................................. A61C 5/14
[52] U.S. Cl. .................................... 433/136; 401/130; 401/196
[58] Field of Search ................. 433/136; 401/196, 130

[56] References Cited

U.S. PATENT DOCUMENTS 2,183,662 12/1939 Worr et al. .......................... 401/196
2,790,984 5/1959 Gilpin .................................. 401/130

Primary Examiner—Robert Peshock

[57] ABSTRACT

This imbiber is to be used, for instance, by dentists for imbibing with a treating liquid a cotton swab held by a cotton plier. The treating liquid is contained in a container having at its upper end a pumping assembly including a piston having an upright piston rod terminated at its top end with an enlarged head formed with a top recess, into which opens a bore formed in the piston and piston rod and communicating with the cylinder of the pump assembly. This cylinder is located within the neck of the container and has at its lower end an intake tube extending close to the bottom of the container. A check valve is mounted in the lower end of the cylinder and a biasing spring urges the piston rod to an upper limit position. By applying with a cotton plier a cotton slab within the recess and depressing the piston with the pliers, the cotton swab becomes soaked with the treating liquid, this being done in a single operation.

5 Claims, 8 Drawing Figures

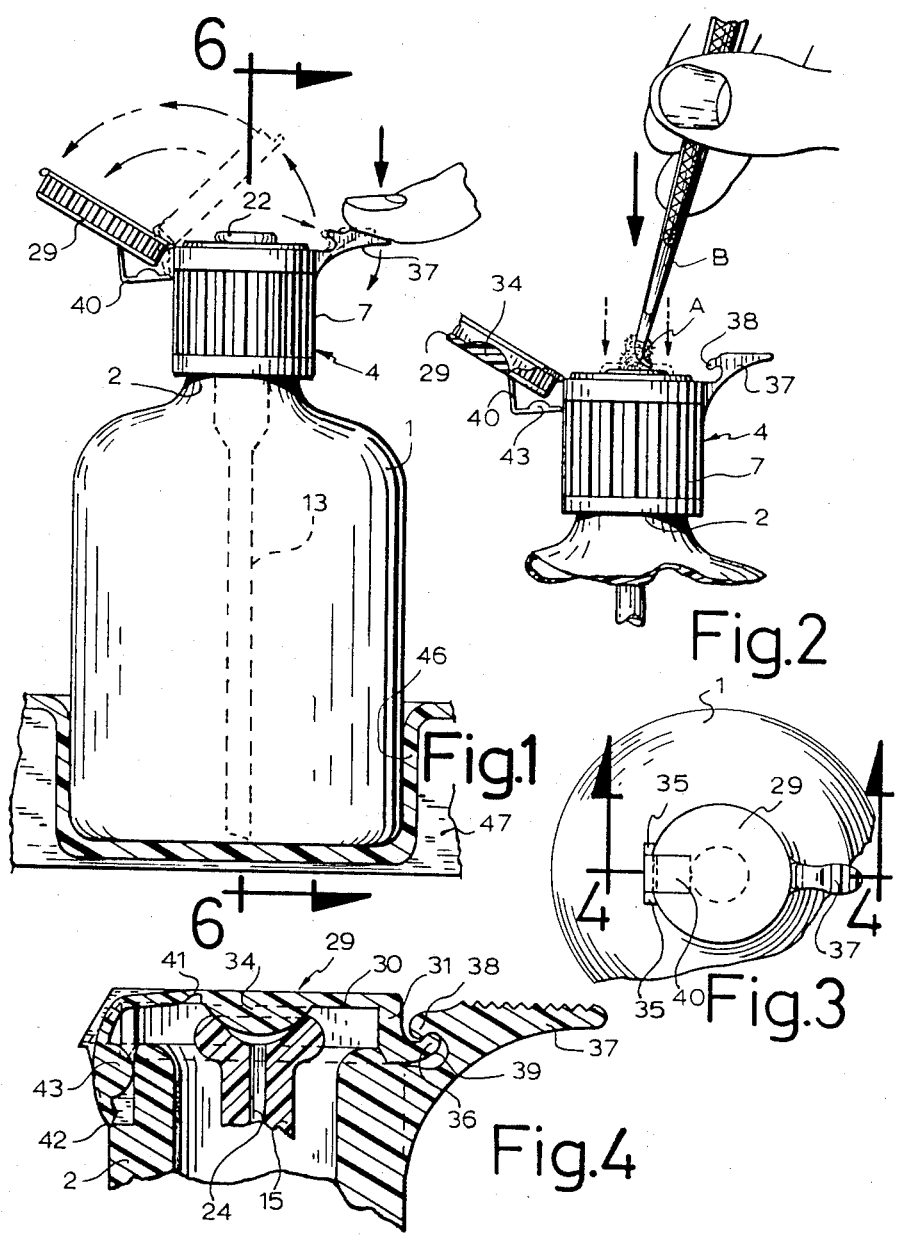

4,540,366

ABSORBENT SWAB IMBIBER

FIELD OF THE INVENTION

The present invention relates to a device for soaking or impregnating with a treating liquid an absorbent swab held at the ends of a plier and adapted to be used by dentists or the like.

BACKGROUND OF THE INVENTION

Photo-polymerizing composites are now used for filling tooth cavities. These composites, once placed within the cavity, are simply exposed to light to harden. This takes a few seconds. However, the cavity must be prepared prior to inserting the photo-sensitive composite. The cavity is first coated with a mixture of a polymer containing calcium hydroxide and a catalyst, in order to protect the nerve of the tooth. Then the cavity surface is coated with an acid for etching said surface, so as to improve the fastening of the filler to the tooth. Then a rather liquid resin material is coated on the cavity surface, in order to make a firm bond between the filler and the tooth. For the last two operations, a conventional method is as follows: the acid and the resin are each enclosed in a small container with a screw cap to prevent evaporation of the treating acid and resin. The dentist must unscrew the cap of the related container, empties a few drops of the treating liquid on a platen and then press a cotton swab onto the liquid on the platen by means of a dentist pliers holding the swab. Then the bottle must again be closed. These are time-consuming operations, especially because two similar treatments must be made for each tooth filling.

OBJECTS OF THE INVENTION

The general object of the invention is to simplify and accelerate the above-noted operation as carried out by a dentist for dental work, such as tooth filling and the like operations where an absorbent swab is required to be soaked into a liquid.

Another object of the invention is to provide a container for the treating liquid which is provided with its own liquid dispensing system, said system designed to dispense the liquid directly onto an absorbent swab held by pliers against the same.

The foregoing and other objects of the present invention will become more apparent during the following disclosure.

SUMMARY OF THE INVENTION

In accordance with the invention, there is provided a container for a treating liquid, said container having an open top neck and a pumping assembly carried by the neck, the pumping assembly including a pump cylinder mounted upright within the neck; an intake tube communicating with the lower end of the pump cylinder and opening close to the bottom of the container, a check valve at the lower end of the pump cylinder only allowing flow of the treating liquid through the intake tube from the container into the pump cylinder, a piston slidable in the pump cylinder, a piston rod fixed to the piston at one end and extending co-axial with the pump cylinder, away from the upper end of the latter, said piston rod having an enlarged head at its upper end defining a top recess, the piston and piston rod having a bore extending therethrough and making communication between the pump cylinder and the recess, piston stroke limiting means and biasing means for biasing the piston and piston rod to an upper limit position in which the top recess is exposed, whereby an absorbent swab can be placed within said recess while held in pliers and pushed to cause depression of said piston rod and piston, so as to cause the liquid already in the pump cylinder to enter the recess and imbibe the absorbent swab.

BRIEF DESCRIPTION OF THE DRAWINGS

In the annexed drawings:

FIG. 1 is an elevation of the imbiber in accordance with the invention as held in a cavity of a service tray, part of which is shown in cross-section;

FIG. 2 is a partial elevation of the top portion of the imbiber showing how an absorbent swab held by pliers is caused to be imbibed with a treating liquid contained in the container;

FIG. 3 is a partial top plan view of the imbiber with the cap in closed position;

FIG. 4 is a vertical section of the top portion of the imbiber with the cap in closed position;

In the drawings, like reference characters indicate like elements throughout.

DETAILED DESCRIPTION OF THE INVENTION

Figure 6:
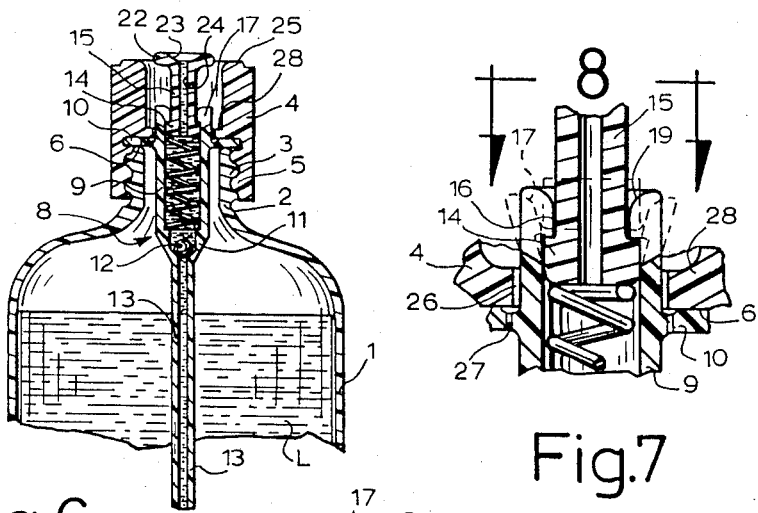
FIG. 6 is a vertical section of the upper part of the imbiber.

A container 1, preferably made of plastic material, has a top open neck 2 with external threads 3, onto which is removably threaded a sleeve member 4 having complementary internal threads 5 at the bottom portion thereof, said threads terminating at their upper ends at a downwardly-facing shoulder 6 (see Fig. 6). The external surface of sleeve member 4 is knurled, as shown at 7, for ease in threading and unthreading the sleeve member 4 on and from the neck 2. A pumping assembly, generally indicated at 8, is carried by the neck 2, being located within the same and extending within the container 1. The pumping assembly 8 comprises a pump cylinder 9 held upright within the neck 2 and co-axial therewith by means of an external flange 10 formed at the upper end of the cylinder 9 (see FIG. 6) and sandwiched between the top face of the neck and the shoulder 6 of the sleeve member 4 when the latter is fully threaded on the neck 2. Obviously, the flange 10 could be permanently adhered to the shoulder 6 of the sleeve member 4. The lower end of the pump cylinder 9 tapers to form a seat 11 for a check valve, namely a ball 12 held by gravity on seat 11 but capable of free upward movement to allow liquid flow in cylinder 9.

Figure 7:
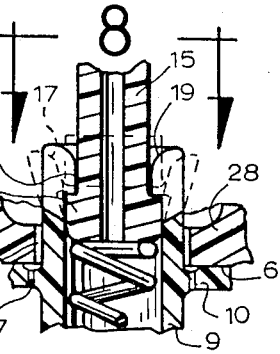
FIG. 7 is a partial vertical section, on an enlarged scale, showing how the piston and piston rod are retained in the upper portion of the pump cylinder.
Figure 8:
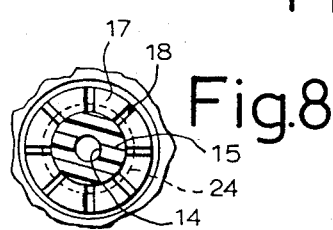
FIG. 8 is a plan section taken along line 8—8 of FIG. 7.

An intake tube 13 can be integrally formed with the lower end of cylinder 9 and extends within the container close to the bottom of the same, as shown in FIG. 1. A piston 14, integrally formed at the lower end of a piston rod 15, is inserted within the cylinder 9 and has a sliding fit therewith. The piston 14 has a greater diameter than that of the piston rod 15 and is retained within the cylinder 9 by radially inward projections 16 (see FIGS. 7 and 8) integrally formed at the upper end of the cylinder 9. These projections are formed by each one of several independent tabs 17 separate from each other by a slot 18. The upper radially inner surface of the tab 17 is rounded, as shown at 19, so that it is easy to insert the piston 14 within the cylinder by simply pressing the same against the rounded surfaces 19 of the tabs 17 to cause radial bending of the tabs, as shown in FIG. 7. The material being resilient, the tabs 17 simply spring back to their original upright position, constituting limiting means to define the upper limit position of the piston 14.

Compression coil spring 20 is inserted within the cylinder 9 and abuts the lower end face of the piston 14 at one end and against an internal shoulder at its other end, said shoulder being formed at the inner surface of the pump cylinder 9 and above the ball 12. Spring 20 biases the piston and piston rod to their upper limit position. The piston rod is formed at its outer upper end with an enlarged head 22 formed with a top recess 23. A bore 24 extends axially through the piston rod 15 and the piston 14, so as to make communication with the inside of the pump cylinder 9 and the recess 23. In the upper limit position of the piston rod, the head 22 is disposed slightly above the level of the top end face 25 of the sleeve member 4. As shown in FIGS. 2 and 6, it will be understood that an absorbent swab A, held by means of a dentist's plier B, can be in one movement pushed against the head 22 within recess 23 to move the piston 14 downwardly, whereby the liquid already filling the pump cylinder 9 and retained therein by the check valve ball 22, is caused to be expelled within the recess 23 and simultaneously imbibes the absorbent swab A. Therefore, the dentist, in a single downward movement, causes the swab A to be soaked with the proper amount of treating liquid L contained in container 1. Upon the return upward stroke of the piston, the swab, already filled with liquid and still retained within the recess 23, is automatically pressed by head 22 under the action of return spring 20, so that the swab A closes the bore 24, whereby piston 14 sucks the liquid held within the container into the cylinder 9 past the check valve ball 12. The intake action is also caused by the fact that the bore 24 has a smaller diameter than that of the internal bore of the intake tube 13.

Any liquid L, which might accidentally spill over the head 22, will fall within the sleeve member 4 and return to the inside of container 1 through registering notches 26 and holes 27 (see FIG. 7) made at the inner edge of the lip 28 defining shoulder 6 and through flange 10 of cylinder 9 respectively.

These registering notches 26 and holes 27 also serve as air intake for the space above the liquid within the container 1. In order to prevent evaporation of the treating liquid and contamination of the same when the imbiber is not in use, a protecting cap 29 is provided. This cap 29 is integrally formed with the sleeve member 4 and is made of a plastic material, as said sleeve member 4. Cap 29 has a flat wall 30 provided at its periphery with a downwardly-extending skirt 31, having at its bottom internal corner a bevelled flat annular portion 32, which in the closed position of the cap, engages an inclined annular step 33 made at the top face 25 of sleeve member 4. This makes a close fit of the cap with the sleeve member and also serves to center the cap 29 with respect to sleeve member 4 and, consequently, with the head 22 in the latter. In the closed position of the cap 29, a central boss 34, formed at the inside surface of flat wall of the cap, makes a tight fit with the outer marginal portion of the top recess 23 of piston rod head 22 (see FIG. 4). The cap 29 is integrally hinged to the sleeve member by means of two circumferentially-spaced thin bridge portions 35 (see FIG. 5). Diametrically opposite these bridge portions 35, the cap has a radially outer tab 36 adapted to lock the cap 29 in closed position by engaging under a latching member 37 formed integral with the sleeve member 4. This latching member 37 is adapted to be depressed by the operator's finger. It is integrally formed with the sleeve member 4, being pliable. It has a rounded nose 38 adapted to be engaged by the inclined underface 39 of the tab 36, so that simple closing of the cap 29 will cause the tab surface 39 to slide over against the nose 38, causing flexing of the latching member 37 and engagement of the nose 38 over tab 36, as shown in FIG. 4.

Means are provided to automatically open the cap 29 upon release of the tab 36 by the latching member 37. These means consist of an L-shape member 40 integrally formed with the cap 29 and sleeve member 4, being connected thereto by means of thin hinge bridging portions 41 and 42, respectively. The hinge portion 42 is disposed below the level of the hinge portions 35 of the cap proper to the sleeve member 4, while the hinge portion 41 is disposed radially inwardly of the skirt and of the hinge portions 35 in the closed position of the cap 29.

The L-shape member 40 is formed as a cut-out from the wall 30 in between the two circumferentially-spaced bridge portions 35. The leg of the L-shape member 40, closest to the hinge 42 of said member to the sleeve member 4, is formed at the inside surface thereof with a boss 43 engageable when the cap 29 is in closed position with the peripheral external surface 44 of a recess 45 made at the upper end of sleeve member 4 between the two bridge portions 35. In the closed position of the cap 29, as shown in FIG. 4, the leg of the L-shape member 40, provided with boss 43, is caused by said boss to become outwardly curved from its normal straight shape. Therefore, it biases the cap to open position in an automatic manner upon release by the latching member 37. This opening force is sufficient to cause the cap to attain the fully-open position shown in FIG. 5. The cap is retained in this fully-open position by the toggle effect of the L-shape member 40 due to the fact that a straight line joining hinge portions 41 and 42 has moved past the hinge portions 35. Therefore, the cap cannot accidentally become closed during use of the imbiber.

Figure 5:
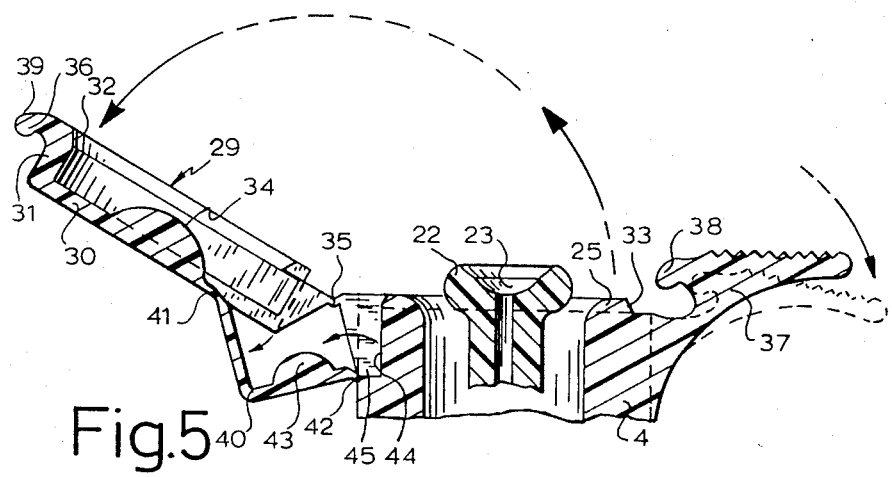
FIG. 5 is a view similar to that of FIG. 4 with the cap in open position.

From the foregoing, it is apparent that it is very simple for the dentists or other dental workers to use the absorbent swab imbiber in accordance with the invention. The container being closed by cap 29, it is a simple matter to first depress the latching member 37, whereby the cap 29 automatically takes his fully-open position, as shown in FIG. 5. Then the cotton swab A is applied by pliers B against the recess 23 of head 22 and the piston 14 pushed down, so as to cause the swab A to absorb the treating liquid L from within the recess 23 of head 22.

The return spring 20 will automatically press the head 22 against swab A when the operator ceases to exert downward pressure on the head 22. During this return movement, the swab closes the bore 24 to cause the refilling of the pump cylinder 9. As shown in FIG. 1, the container 1 will normally have a small size, for instance a capacity of a few milliliters, and can be easily retained in upright position by insertion within a conforming recess 46 formed in a service tray 47, as normally used by dentists and placed on a normal service tray held beside a dentist chair.

What I claim is:

1. An absorbent swab imbiber for dental work and the like, comprising a liquid container having an open top neck, a pumping assembly carried by said neck, said assembly comprising a pump cylinder mounted upright within said neck, an intake tube communicating with the lower end of said pump cylinder and opening close to the bottom of said container, a check value at the lower end of said pump cylinder only allowing flow of said liquid through said intake tube from said container into said pump cylinder, a piston rod fixed to said piston at one end and extending coaxial with said pump cylinder upwardly from the upper end of the latter, said piston rod having an enlarged head at its outer end defining a top recess, said piston and piston rod having a bore extending therethrough and making communication between said pump cylinder and said recess, piston stroke limiting means; biasing means biasing said piston and piston rod to an upper limit position in which said top recess is exposed, whereby an absorbent swab can be placed within said recess and pushed to cause depression of said piston rod and piston, so as to cause said liquid already in said pump cylinder to enter said recess and imbibe said absorbent swab; a sleeve member, carried by said neck and surrounding said piston rod, with said head exposed at the top of said sleeve member in the upper limit position of said piston; a cap, removably closing the top end of said sleeve member and overlying said head and having a top wall making a sealing contact with said recess exteriorly of said bore in the closed position of said cap and with said piston in said upper limit position; hinge means between said cap and said sleeve member, whereby said cap can be pivotally moved from open to closed position; latch means disposed diametrically opposite to said hinge means and carried by said sleeve member to engage and latch said cap in closed position; biasing means, automatically causing opening movement of said cap to fully open position upon release of said latching means; said sealing contact being obtained by a boss formed at the inside surface of the top wall of said cap and conforming to the marginal radially external portion of said recess; means being formed on said cap and on the top end of said sleeve member, to center said cap with respect to said sleeve member in the closed position of said cap; wherein said latching means includes a latching member, integrally formed with said sleeve member and diametrically opposite said hinge means; said latching member having a radially-inwardly directed nose; said cap member having a radially-outwardly directed tab at its periphery, said tab being engageable under said nose in the closed position of said cap member; said latching means being made of a flexible material so that one is able to release said nose from said tab, thereby releasing said cap member for its opening.

2. An imbiber as claimed in claim 1, wherein said biasing means to cause automatic opening movement of said cover include an L-shaped member hinged to said sleeve member at one end and to said cover at its other end at points respectively below and radially inwardly of said hinge means connecting said cap to said sleeve member, said L-shape member being made of flexible material and the leg of said L-shape member directly connected to said sleeve member being provided at its inner face with a boss engageable with a peripheral external surface of said sleeve member in the closed position of said cap to cause flexing of said last-named leg; then biasing said cap towards opening position, said cap being resiliently retained in said open position by the toggle effect of the hinge connections of said L-shape member with respect to the hinge means of said cap on said sleeve member.

3. An imbiber as claimed in claim 1, wherein said piston has a greater diameter than that of said piston rod and said limiting means consist of radially inward projections formed at the upper end of said pump cylinder and abutting against said piston in the upper limit position of the latter.

4. An imbiber as defined in claim 3, wherein said projections are formed on a plurality of independent resilient tabs integrally formed at the upper end of said pump cylinder and radially outwardly flexible to release said piston from within said pump cylinder.

5. An absorbent swab imbiber for dental work and the like, comprising a liquid container having an open top neck, a pumping assembly carried by said neck, said assembly comprising a pump cylinder mounted upright within said neck, an intake tube communicating with the lower end of said pump cylinder and opening close to the bottom of said container, a check valve at the lower end of said pump cylinder only allowing flow of said liquid through said intake tube from said container into said pump cylinder, a piston slidable within said pump cylinder, a piston rod fixed to said piston at one end and extending co-axial with said pump cylinder upwardly from the upper end of the latter, said piston rod having an enlarged head at its outer end defining a top recess, said piston and piston rod having a bore extending therethrough and making communication between said pump cylinder and said recess, piston stroke limiting means; biasing means biasing said piston and piston rod to an upper limit position in which said top recess is exposed, whereby an absorbent swab can be placed within said recess and pushed to cause depression of said piston rod and piston, so as to cause said liquid already in said pump cylinder to enter said recess and imbibe said absorbent swab; said piston having a greater diameter than that of said piston rod and said limiting means consist of radially inward projections formed at the upper end of said pump cylinder and abutting against said piston in the upper limit position of the latter; wherein said projections are formed on a plurality of independent resilient tabs integrally formed at the upper end of said pump cylinder and radially outwardly flexible to release said piston from within said pump cylinder.

* * * * *